United States Patent [19]

Ross

[11] Patent Number: 4,744,755
[45] Date of Patent: May 17, 1988

[54] DENTAL IMPLANT AND METHOD FOR INSTALLING SAME

[75] Inventor: Stanley E. Ross, Boca Raton, Fla.

[73] Assignee: Ross Systems Corporation, Palm Beach, Fla.

[21] Appl. No.: 896,524

[22] Filed: Aug. 13, 1986

[51] Int. Cl.$^4$ .............................................. A61C 8/00
[52] U.S. Cl. .................................. 433/173; 433/201.1
[58] Field of Search .............. 433/173, 174, 175, 176, 433/220, 221, 193, 201.1, 210, 213, 214, 223, 195; 264/16, 19

[56] References Cited

U.S. PATENT DOCUMENTS

| | | | |
|---|---|---|---|
| 711,324 | 10/1902 | Lacy | 433/173 |
| 866,304 | 9/1907 | Roach | 433/177 |
| 3,499,222 | 10/1970 | Linkow et al. | 433/174 |
| 3,579,830 | 5/1971 | Morel | 433/174 |
| 3,729,825 | 5/1973 | Linkow et al. | 433/176 |
| 3,797,113 | 3/1974 | Brainin | 433/173 |
| 4,065,817 | 1/1978 | Branemark et al. | 3/1.91 |
| 4,180,910 | 1/1980 | Straumann et al. | 433/173 |
| 4,185,383 | 1/1980 | Heimke et al. | 433/173 |
| 4,231,120 | 11/1980 | Day | 433/173 |
| 4,304,553 | 12/1981 | Heimke et al. | 433/173 |
| 4,359,318 | 11/1982 | Gittleman | 433/173 |
| 4,431,416 | 2/1984 | Niznick | 433/174 |
| 4,439,152 | 3/1984 | Small | 433/173 |
| 4,488,875 | 12/1984 | Niznick | 433/173 |
| 4,531,915 | 7/1985 | Tatum, Jr. | 433/173 |

FOREIGN PATENT DOCUMENTS 1291470 10/1972 United Kingdom.
1352188 5/1974 United Kingdom.

OTHER PUBLICATIONS

"A 15-Year Study of Osseointegrated Implants in the Treatment of the Edentulous Jaw", Adell et al, 1981, vol. 10, pp. 387-416.

Primary Examiner—John J. Wilson
Attorney, Agent, or Firm—Burns, Doane, Swecker & Mathis

[57] ABSTRACT

A dental implant is adapted to be installed in a pre-drilled bore formed in jaw bone tissue for retaining a dental prosthesis. The implant comprises a generally cylindrical body defining a longitudinal axis and including an outer periphery. The body is open at a front end thereof and includes a front cylindrical cavity for receiving a cylindrical bone core. A plurality of through-holes is formed in the body and communicates with the front cavity to accommodate the growth of bone tissue therethrough. The body is open at a rear end thereof and includes a rear cavity communicating with the open rear end for receiving a prosthesis attachment. The outer periphery of the body includes a plurality of longitudinally spaced, reservoir-defining structures, each of which includes a recessed surface facing toward one of the longitudinal ends of the implant and arranged to store blood adjacent the surrounding bone to promote the growth of new bone tissue.

13 Claims, 4 Drawing Sheets

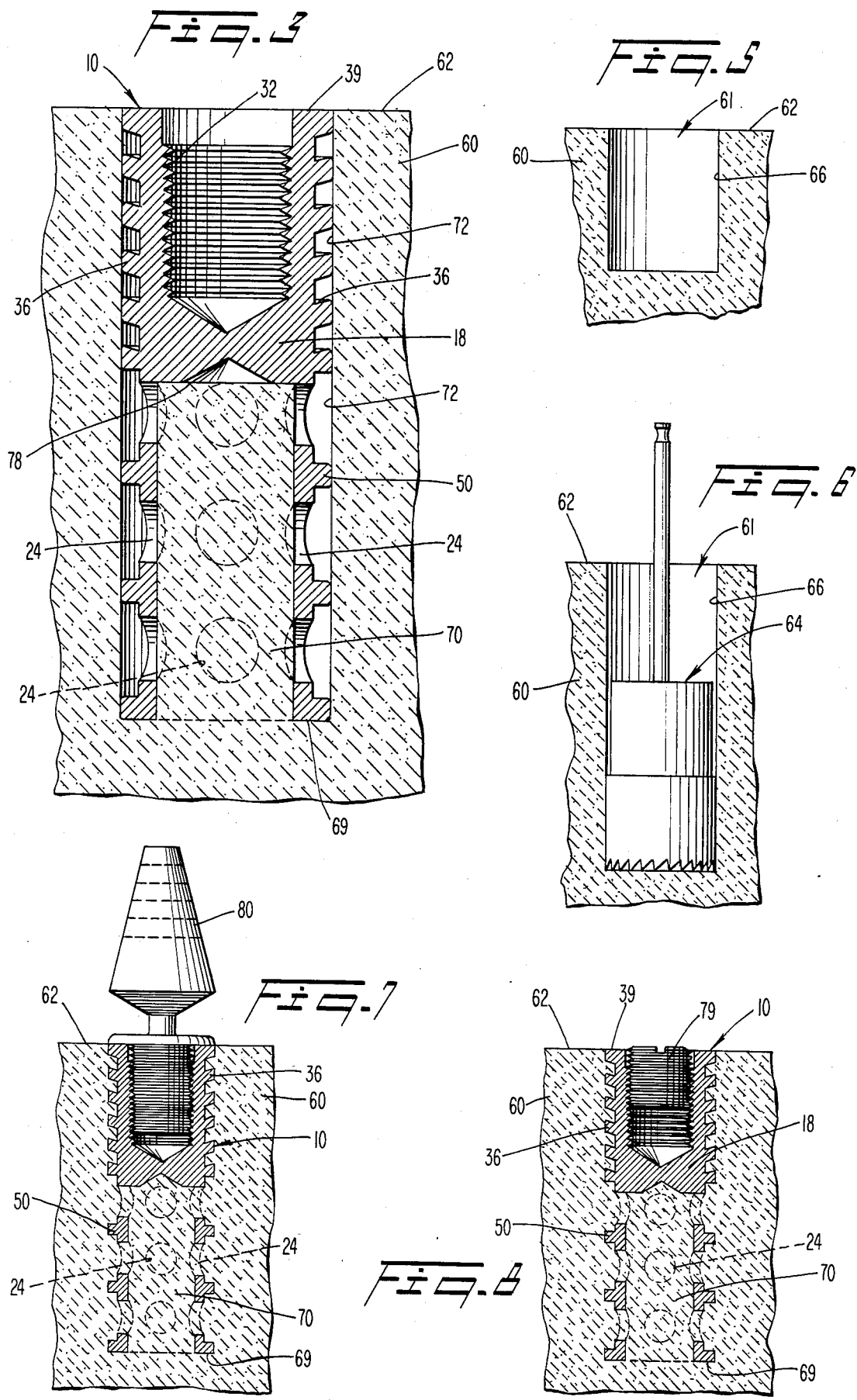

DENTAL IMPLANT AND METHOD FOR INSTALLING SAME

RELATED INVENTION

Attention is directed to a related invention of the present inventor disclosed in concurrently filed U.S. application Ser. No. 06/896,101.

BACKGROUND AND OBJECTS OF THE INVENTION

The present invention relates to dental implants which are adapted to be anchored in bone tissue to secure dental prostheses within the mouth. The invention also relates to methods for installing such inserts into bone tissue.

It has been proposed to secure dental prostheses within a patient's mouth by affixing the prostheses to dental implants which are embedded directly within the jaw bone. The implants and embedding techniques heretofore proposed and utilized in practice have not met with universal acceptance among dental practitioners due to considerable limitations regarding the placement of the implants within the mouth and/or uncertainties as to the useful lifespan of the implants.

In that regard, one currently employed technique involves the use of an implant 1 (depicted in FIGS. 12–14 of the accompanying drawings) having external threads 2 by means of which the implant is to be screwed into the bone tissue 3. A bore is first drilled into the bone tissue, the bore having a diameter less than the maximum diameter of the threads of the implant. By screwing the insert 1 into the bore, the threads 2 cut into the bone tissue 3. Variations of such a technique are disclosed in U.S. Pat. Nos. 3,499,222 and 4,431,416 and British Pat. Specification GB No. 1,291,470 published Oct. 4, 1972.

However, such a technique can result in so-called "saucerization" wherein some of the bone tissue does not grow back against the implant, i.e., areas between the bone and implant are occupied by soft tissue 4 which does not contribute appreciably to the anchoring of the implant. In cases where implants have been installed in the lower jaw bone, saucerization has been observed to occur at the upper end of the bore. Such saucerized areas can become infected, leading to a spreading of the saucerization along the implant whereby the securement of the implant is significantly undermined.

Although the exact causes of saucerization are not yet known for certain, it is the belief of the present inventor that because of the harsh treatment to which the bone is subjected during implant installation, the rate at which the bone is able to regenerate and grow against the implant is deterred to such an extent that soft gum tissue 4 is able to grow into and occupy the space between the implant 1 and the bone 3 at the open end of the bore. That deterred growth rate may result from a number of factors, including the severe traumatizing of the bone as it is cut and fractured along the region 3A by the self-tapping threads of the implant, and/or the likelihood that the bone is deprived of blood at least at that portion of the bone located at the top of a bore in the lower jaw since blood tends to gravitate away from that bone portion. In that regard, it is well known that blood, once it clots, will develop fibroblasts and osteoblasts which promote the development of bone tissue. By depriving the bone tissue of an ample blood supply, the regeneration and regrowth of bone tissue will be retarded, thereby permitting soft gum tissue to enter the area between the implant and bone. If such saucerization occurs and spreads along the length of the implant, the lifespan of the implant can be significantly shortened.

Some dental practitioners install more than the required number of implants into the bone, whereby the extra implants are kept available as "spares" in the event that the active implant(s) become dislodged from the bone. Besides being more expensive and inconvenient to the patient, that practice is only feasible in cases involving the installation of a relatively long prosthesis wherein the space between the active implant(s) is large enough to accommodate the "spare" implants.

In order to augment the anchoring of the implant, the implant can be provided with a hollow front end which receives a core 5 of the bone (FIG. 13). Such an expedient, disclosed for example in U.S. Pat. Nos. 3,499,222; 4,180,910; 4,359,318; and 4,431,416, involves the cutting of an annular kerf in the bone tissue to leave a cylindrical core of bone surrounded by the kerf. The open front end of the implant receives the core as the implant is inserted into the kerf. The wall of the implant surrounding the core is provided with holes 6 to enable bone tissue to grow through the holes. In the case of implants which include self-tapping screw threads 2, however, the screwing-in of the implant may impose sufficient lateral stresses on the core to cause the core to be broken-off at its base. Even if the core is eventually able to regenerate and regrow, the overall anchoring process could be delayed.

Furthermore, the act of screwing-in a self-tapping implant requires substantial torque imposed by means of a ratchet wrench which mates with a wrench-receiving socket 7 of the implant (FIG. 14). However, such wrenches are relatively large and cumbersome and require a relatively large amount of space to accommodate tool manipulation. Consequently, such implants are not suitable for use in the back portions of a patient's mouth where there exists little room to turn the handle of the wrench, or in narrow areas between existing teeth which are not large enough to accommodate the head of the wrench.

In addition, the fracturing of bone tissue caused by the screw threads renders the implants unsuitable for use in areas of exceptionally thin bone. Therefore, in cases where a patient's bone has been diminished in thickness due to surgical operation, injury, etc., the use of a screw-in type implant may not be feasible.

Therefore, it will be appreciated that for at least the above-discussed reasons, the overall utility and versatility of screw-in type implants has been significantly limited.

It has also been proposed to pre-form female screw threads in the bone by means of a thread-forming drill, rather than by the use of self-tapping threads on the implant. Such a technique is disclosed in a article entitled "A 15-Year Study of Osseointegrated Implants in the Treatment of the Edentulous Jaw" by Adell, Lekholm, Rockler, and Branemark, published in the International Journal of Oral Surgery, Munksgaard, Copenhagen, 1981, Vol. 10, pp. 387–416. In that technique, the thread-forming drill does not leave a core in the bore to augment the anchoring action. Also, the drill is designed to form a widening at the mouth of the bore to accommodate the insertion of an implant having an enlarged collar at is outer end. In practice, saucerization results from the formation of such an widening, and the saucerization gradually spreads, e g., by about 0.10 mm per year along the length of the implant according to the above-referenced article. Once a sufficient length of saucerization has occurred, the implant will be inadequately anchored. It should further be noted that even though the female threads are predrilled in the bore, the threads on the implant are intended to be partly self-tapping. Thus, a wrench is needed, whereby the areas of the mouth in which that implant can be employed are limited, and a certain amount of bone fracture and bone trauma will likely occur during installation of the implant.

It is, therefore, an object of the present invention to minimize or obviate problems of the types discussed above.

A further object is to provide dental implants and methods for installation thereof which minimize bone fracturing and traumatization and resist the occurrence of saucerization.

Another object is to provide such methods and apparatus which promote the regeneration and regrowth of surrounding bone tissue.

A further object is to provide such methods and apparatus which enable the implant to be installed in confined and narrow areas of the mouth and in thin bone tissue.

Yet another object is to enable an implant to be installed without the need for cement or wrenches.

An additional object is to promote the retention of blood and blood clots adjacent the cut bone tissue to promote the regeneration and growth of that bone tissue.

Still another object is to provide a hollow implant which fits over a bone core and which can be installed without an appreciable risk of breaking the core.

SUMMARY OF THE INVENTION

These objects are achieved by the present invention which relates to a dental implant adapted to be installed in a predrilled bore formed in jaw bone tissue for retaining a dental prothesis. The implant comprises a generally cylindrical body defining a longitudinal axis and including an outer periphery. The body is open at a front longitudinal end thereof and includes a front cylindrical cavity communicating with the open front end for receiving a cylindrical bone core. A plurality of through-holes is formed in the body and communicates with the front cavity to accommodate the growth of bone tissue therethrough. The body is opened at a rear longitudinal end thereof and includes a rear cavity communicating with the open rear end for receiving a prothesis attachment. A plurality of longitudinally spaced reservoir-defining structures is formed in the outer periphery. Each of those structures includes a recessed surface facing generally toward one of the longitudinal ends of the implant and is arranged to store blood adjacent to surrounding bone tissue.

Preferably, a plurality of longitudinally spaced, circumferentially extending grooves is formed in the outer periphery to define longitudinally spaced, circumferentially disposed ribs including circumferentially continuous outer peripheries of equal diameter. The ribs each include a front surface facing toward the front end of the implant and a rear surface facing toward the rear end. At least one of those surfaces is offset longitudinally relative to the outer periphery of the rib in a direction away from the respective implant end toward which such one surface faces. Consequently, the offset surface defines the annular reservoir.

In implants adapted to be installed in a lower jaw bone, the reservoirs face toward the rear end. In implants adapted to be installed in an upper jaw bone, the reservoirs face toward the front end. Alternatively, reservoirs could be provided at both surfaces of each rib to adapt a single implant design for use in upper and lower jaw bones.

The invention also relates to a method for installing such implants.

BRIEF DESCRIPTION OF THE DRAWINGS

The objects and advantages of the invention will become apparent from the following detailed description of a preferred embodiment thereof in connection with the accompanying drawings in which like numerals designate like elements, and in which:

FIG. 3 is a view similar to FIG. 2 after the implant has been pushed into a predrilled bore;

FIGS. 5 and 6 are schematic views representing steps involved in installing the implant in bone tissue;

FIG. 7 is a view similar to FIG. 3 with the implant containing a prosthesis-retaining member;

FIG. 8 is a view similar to FIG. 7 with the implant containing a retaining screw;

DETAILED DESCRIPTION OF PREFERRED EMBODIMENTS OF THE INVENTION

Figure 1:
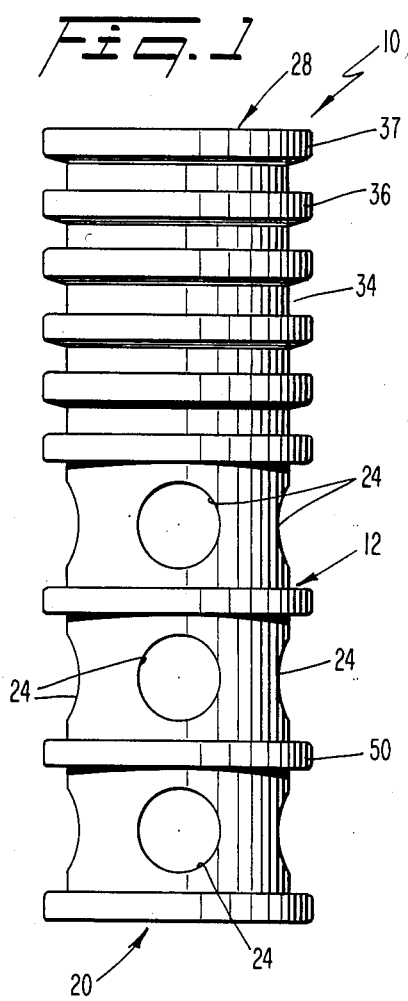
FIG. 1 is a side elevational view of an implant according to the present invention.
Figure 2:
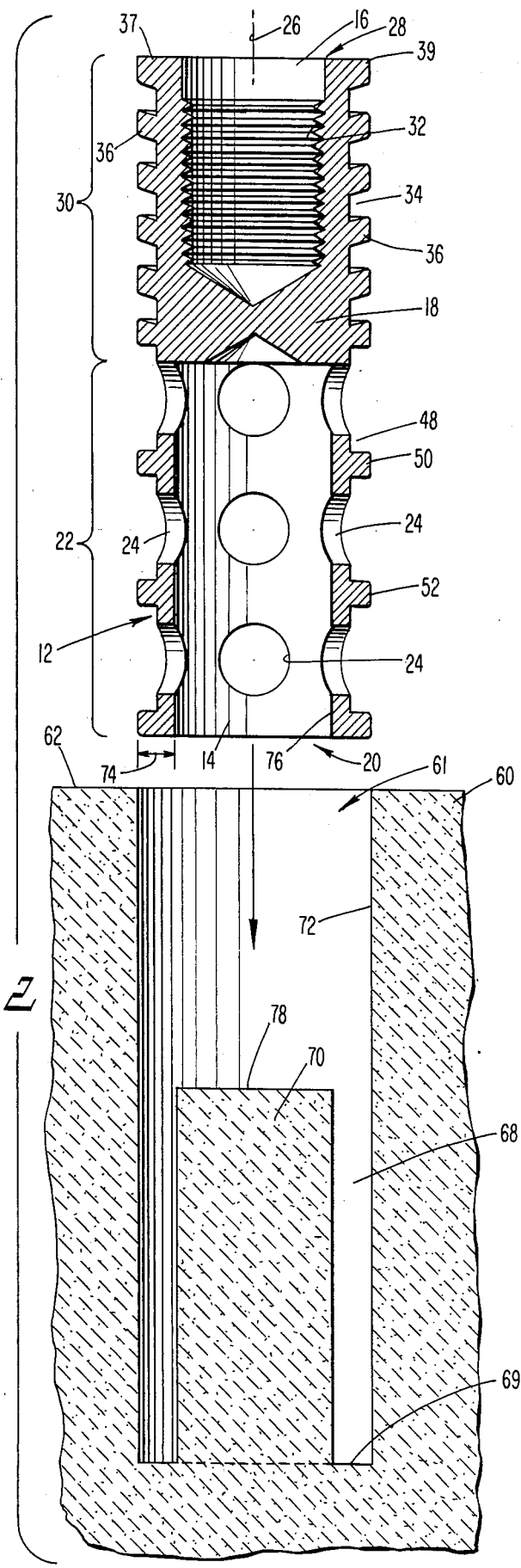
FIG. 2 is a longitudinal sectional view taken through the implant and depicting the implant as it is being inserted into a bore formed in jaw bone tissue.
Figure 4:
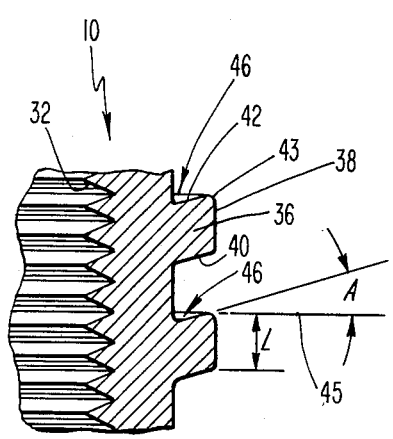
FIG. 4 is an enlarged fragmentary view of the implant depicting the recessed nature of the rear surfaces of the ribs.

A dental implant 10 according to the present invention, depicted in FIGS. 1-8, is suitable for use in lower jaw bones. The implant comprises a generally cylindrical body 12 formed of a biocompatable material such as, for example, titanium such as commercially pure titanium or a titanium alloy such as Ti 6AL 4V, or other equivalent materials as will be apparent to those skilled in the art. The body defines front and rear circular cylindrical cavities 14, 16 which are separated by a divider wall 18 (FIG. 2). The front cavity 14 is open toward a front end 20 of the body 12 and is surrounded by a front portion 22 of the body. That front portion 22 is apertured by means of a plurality of through-holes 24. The through-holes are arranged in circumferential rows, each row being spaced apart in a direction parallel to the longitudinal axis 26 of the body.

The rear cavity 16 opens toward a rear end 28 of the body 12 and is surrounded by a rear portion 30 of the body. That rear portion 30 is non-apertured, i.e., it does not afford any appreciable external communication for the rear cavity except via the rear opening 28. The rear cavity includes an internal wall which contains female screw threads 32.

The exterior of the rear portion 30 comprises a plurality of longitudinally alternating grooves 34 and ribs 36. The ribs 36 are circular and extend circumferentially continuously around the body 12. Each rib includes an outer peripheral surface 38 which extends circumferentially continuously. That is, the surface 38 is circular as opposed to being helical as in the case of screw threads. Also, the surface 38 has a dimension L in the longitudinal direction. Front and rear edges of the surface 38 are slightly radiused. The outer surfaces 38 are of equal outer diameter and define the outer periphery of the rear portion 30.

Each rib lies in a plane extending transversely to the axis 26 and includes front-facing and rear-facing surfaces 40, 42 which are circumferentially continuous. The rear surface 42 is recessed, e.g., preferably offset forwardly relative to a rear edge 43 of the rib outer periphery 38 (which rear edge 43 defines the outer circumference of the surface 42) to define an annular reservoir 46 adapted to store a quantity of blood. Accordingly, a supply of blood will be made continuously available to the bone tissue situated adjacent the reservoirs. The presence of the blood adjacent the bone tissue will lead to the formation of organized blood clots which, in turn, will lead to the development of the necessary cells for bone formation such as fibroblasts and osteoblasts to promote the rapid formation and growth of new bone tissue.

Preferably, the recessing of the rear surface 42 is created by inclining the rear surface 42 forwardly obliquely from the rear edge 43 of the outer periphery 38 of the rib. Thus, the radially innermost edge of the rear surface 42 is disposed forwardly of the edge 43. The rear surface 42 is thus inclined at an angle A relative to a plane 45 oriented perpendicularly to the longitudinal axis 26. Preferably, that angle A is from ten to sixty degrees, most preferably about fifteen degrees.

The rib 37 located at the rear end of the implant does not form a reservoir, but rather has a front face 39 which is flush with the rear end of the implant and extends perpendicularly to the longitudinal axis so as to completely close-off the mouth of the bore and prevent the growth of soft gum tissue into the bore.

The exterior of the front portion 22 of the body 12 includes longitudinally alternating grooves 48 and ribs 50. The through-holes 24 are formed in the bases of the grooves 48. Each rib 50 includes an outer peripheral surface 52, the diameter of which is equal to that of the outer surfaces 38 of the ribs 36 on the rear portion 30. It will thus be appreciated that the outer surfaces 52, 38 define the outer peripheries of the front and rear portions 22, 30, respectively, as well as the maximum outer diameter of the implant.

The ribs 50 on the front portion 22 may, if desired, include forwardly offset rear surfaces similar to those discussed earlier herein in connection with the ribs 36 of the rear portion 30, so as to define blood-retaining reservoirs. However, ribs of the reservoir-defining type are of greater dimension in the longitudinal direction, and thus would reduce the number of through-holes 24 which could be employed. It is preferable to maximize the number of through-holes since they accommodate the growth of bone tissue through the body to anchor the body in the jaw bone. Furthermore, the need to store blood at the front portion 22 of the body 12 may be less critical than at the rear portion 30 since blood gravitates away from the mouth of a bore formed in the lower jaw bone.

The implant 10 is installed in accordance with the following procedure. The gum tissue overlying the area of the lower jaw bone 60 in which the implant is to be affixed is cut and folded back to expose the bone surface 62. A circular cylindrical bore 61 is then formed in the bone. This can be performed in stages in accordance with a conventional technique wherein a trephine drill 64 cuts a circular kerf in the bone to form an expendable core of bone. That expendable core of bone is removed to leave a cylindrical hole 66 as depicted in FIG. 5. The drill 64 is then further advanced into the bone (FIG. 6) to create an additional kerf 68 (FIG. 2) which, in turn, defines a circular cylindrical permanent core 70. The bore now contains a circular cylindrical inner wall 72 of uniform diameter from the bone surface 62 to the base 69 of the kerf 68. The drill size is selected such that the diameter of the wall 72 corresponds to the diameter of the outer surfaces 38, 52 of the ribs 36, 50, and such that the radial thickness of the kerf 68 corresponds to the radial thickness 74 (FIG. 2) of the front portion 22, i.e., the thickness from an inner wall 76 of the front cavity to the outer surfaces 52 of the ribs 50. Thus, the outer diameter of the permanent core 70 corresponds to the diameter of the inner wall 76 of the front cavity 14.

In addition, the longitudinal distance from the end face 78 of the core 70 to the jaw bone surface 62 is equal to the sum of the longitudinal thickness of the divider wall 18 and the longitudinal dimension of the rear cavity 16. Furthermore, the longitudinal dimension of the kerf 68 is at least equal to that of the front cavity 14.

The implant is installed by being pushed, front end first, into the bore 61, preferably by hand and without the need of a wrench. Due to the above-described dimensional relationships, the outer periphery of the body, as defined by the outer surfaces 38, 52 of the ribs, will slide frictionally along the inner wall 72 of the bore, and the front cavity 14 will telescopingly receive the core 70 as the inner wall 76 of the front cavity slides frictionally along the outer peripheral surface of the core.

Therefore, once pushed-in, the implant will be snugly held within the bore (FIG. 3). This is achieved without cracking or traumatizing the bone and without breaking the core 70. Hence, no undue delays in the initiation of bone regrowth will occur. Furthermore, since the circumferentially uninterrupted outer surfaces 38, 52 engage the wall 72 of the bore or at least are in immediate proximity to the wall 72, the tendency for blood to gravitate along the wall 72 will be resisted, thereby promoting the formation of blood clots. Importantly, blood will be stored within the reservoirs 46 and will begin to clot. The accumulation and retention of blood clots in the immediate vicinity of bone tissue promotes the formation of organized blood clots which, in turn, leads to the development of the necessary cells for bone formation, such as fibroblasts and osteoblasts. As a result, the regeneration and regrowth of the bone tissue is promoted. Thus, it is assured that such bone regrowth will not only occur, but will occur rapidly without undue delay. Accordingly, the healing process will be accelerated.

Figure 13:
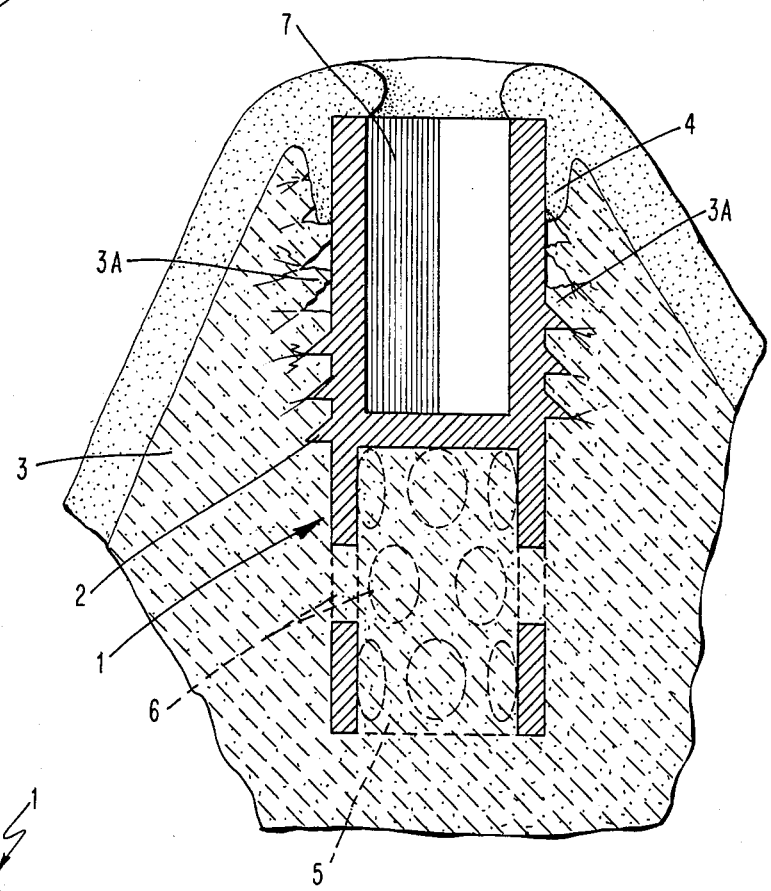
FIG. 13 is a cross-sectional view of the FIG. 12 implant after it has been screwed into a jaw bone.
Figure 14:
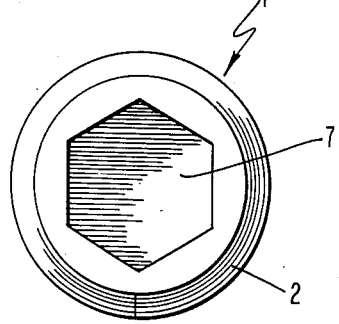
FIG. 14 is a top view of the FIG. 12 implant.

As noted earlier herein, the lack of blood available to bone tissue may not only retard bone regrowth, but may even result in an absence of bone regrowth in the blood-deprived areas as soft tissue grows into the areas between the bone and implant. One such area, for example, depicted at 4 in FIG. 13, is situated at the mouth of a bore formed in the lower jaw bone since blood will flow from that area gravitationally. However, the presence of blood reservoirs 46 in the rear portion of the implant eliminates the possibility that the bone tissue near the mouth of the bore will be deprived of blood, but rather insures that an ample supply of blood and blood clots will be provided. Furthermore, since the bone is not fractured by the implant (in contrast to implants employing self-tapping threads), the implant will be in contact with healthy bone and thus will be capable of resisting dislodgement of the implant. Also, no spaces will be created into which soft tissue may grow. The rearwardmost rib 37 aids in closing-off the mouth of the bore.

Very quickly, then, the bone tissue located externally around the implant and internally within in the front cavity 14 will grow toward the implant and become adhered thereto (i.e., adherence occurs since the implant is formed of a biocompatable material). Bone tissue will also grow into the grooves 34, 48 between the ribs 36, 50 and through the through-holes 24 to strongly resist dislodgement of the implant.

At the time when the implant is pushed into the bore 61, the rear cavity 16 preferably contains a threaded retaining pin 79 (also formed of the afore-described biocompatible material) to prevent the entry of foreign matter into the rear cavity (see FIG. 8). After the healing process has progressed sufficiently, the retaining pin can be removed and eventually replaced by a threaded insert 80 (depicted in FIG. 7) to which a dental prosthesis (not shown) may be attached. Therefore, the implant and insert 80 are both installed without the use of cement.

Figure 9:
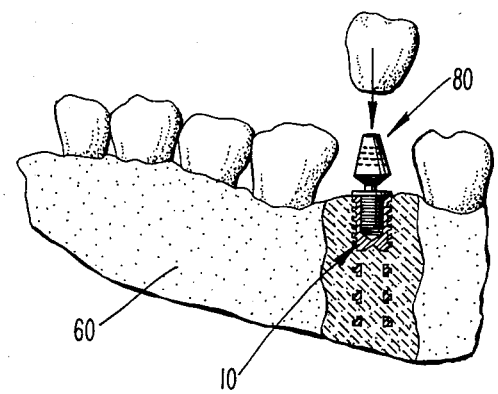
FIG. 9 is a view of the insert in place between a pair of teeth in the jaw.

Since there is no need to screw-in the implant via self-tapping screw threads, there is no need to employ a wrench. Hence, the implant can be easily installed in back areas of the mouth. Also, the implant can be inserted into any space which is large enough to receive a single tooth (see FIG. 9), i.e., the implant is not restricted to use only in spaces large enough to accommodate the head of a wrench.

The implant 10 can be utilized in both the upper and lower jaw bones, but it is preferably employed in the lower jaw bone since the ribs will form reservoirs to store blood.

Figure 10:
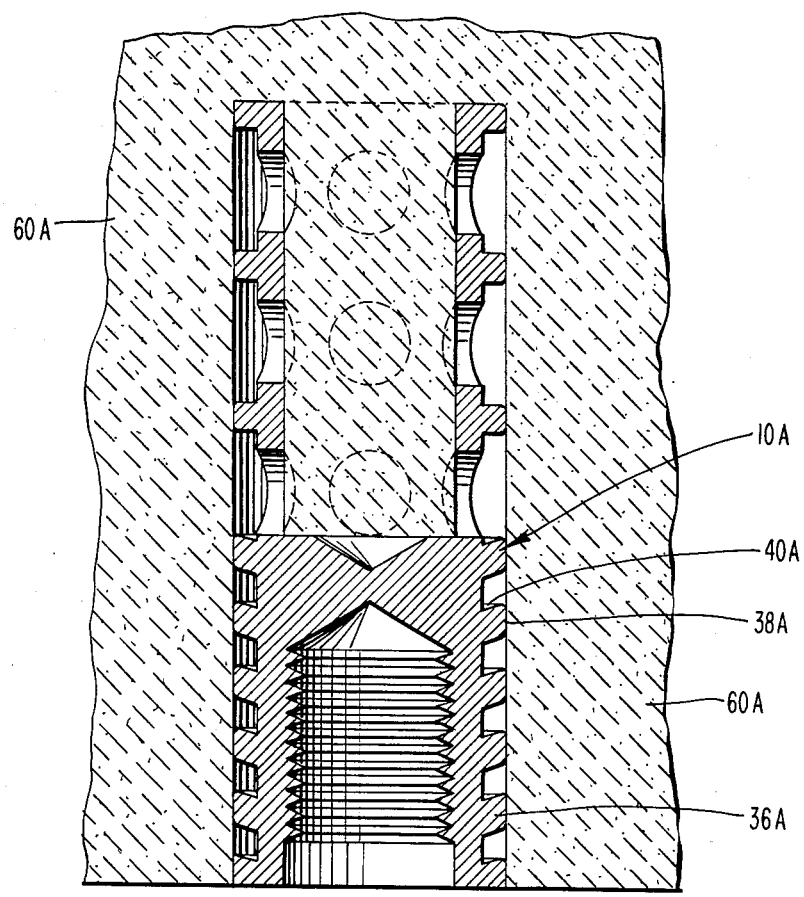
FIG. 10 is a view similar to FIG. 3 of a modified form of implant suitable for use in upper jaw bones.
Figure 12:
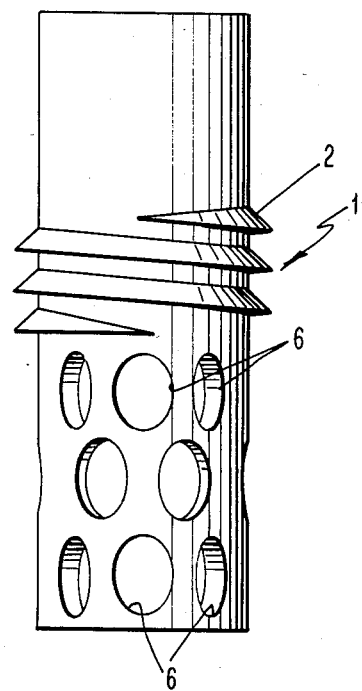
FIG. 12 is a side elevational view of a prior art implant.

An implant 10A more suitable for use in an upper jaw bone 60A is depicted in FIG. 10. That implant is similar to the implant 10 described in connection with FIGS. 1-8 except that the reservoir-forming ribs 36A are inclined in the opposite direction. That is, the front surface 40A is inclined rearwardly from the front end of the outer peripheral surface 38A of the rib. Hence, the reservoirs face toward the front end of the implant. The angle of inclination of the surface 40A can be the same as that described earlier with reference to reservoirs 46.

Figure 11:
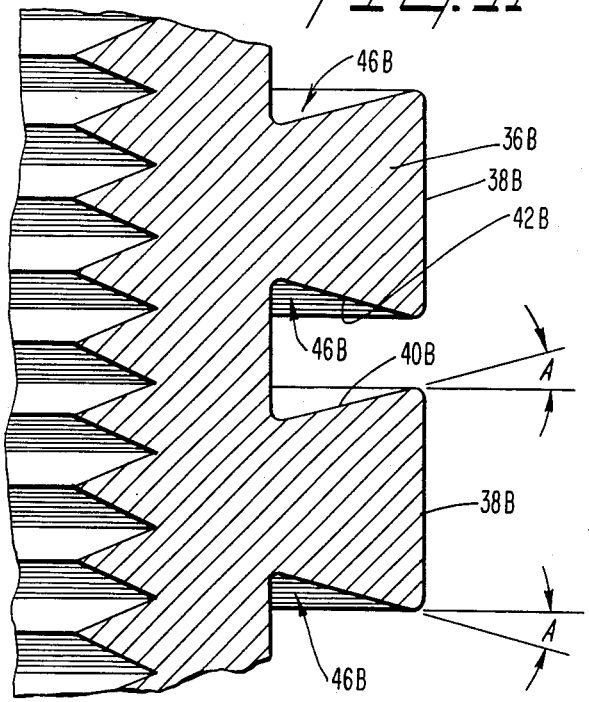
FIG. 11 is a view similar to FIG. 4 of yet another rib configuration.

Yet another implant configuration is depicted in FIG. 11, wherein both rib surfaces 40B, 42B are offset longitudinally relative to the rib outer periphery 38B in a direction away from the implant ends toward which they face. Accordingly, such an implant defines reservoirs 46B facing forwardly and rearwardly and can be used in either the upper or lower jaw bone.

Although the present invention has been described in connection with a preferred embodiment thereof, it will be appreciated by those skilled in the art that modifications, additions, substitutions, and deletions not specifically described may be made without departing from the spirit and scope of the invention as defined in the appended claims.

What I claim is:

1. A dental implant adapted to be installed in a pre-drilled bore formed in jaw bone tissue for retaining a dental prosthesis, said implant comprising a generally cylindrical body defining a longitudinal axis, said body being open at a front end thereof and including a cylindrical front cavity communicating with said open front end for receiving a cylindrical bone core, said front cavity being surrounded by a front portion of said body, said front portion including a plurality of circumferentially and radially spaced through-holes extending radially completely therethrough to accommodate the growth of bone tissue therethrough, said body being open at a rear end thereof and including an internally threaded cylindrical rear cavity which communicates with said open rear end and adapts said rear cavity to receive externally threaded prosthesis-attachment means, said rear cavity being surrounded by a rear portion of said body, said rear portion being non-apertured, said front and rear portions of said body including front and rear outer peripheries, respectively, each of which including a plurality of outwardly projecting longitudinally spaced, circumferentially extending ribs, each rib lying in a plane extending transversely to said longitudinal axis, at least some of said ribs on said rear outer periphery surrounding said rear cavity, said ribs on said front and rear outer peripheries including outer surfaces of the same diameter to define a maximum outer diameter of said implant, at least some of said ribs including a front surface facing toward said front end and a rear surface facing toward said rear end, at least one of said front and rear surfaces being offset longitudinally relative to said outer periphery of said rib in a direction away from the respective implant end toward which said one surface faces in order to define an annular reservoir adapted to store blood adjacent to surrounding bone tissue.

2. A dental implant according to claim 1, wherein said at least one surface comprises said front surface.

3. A dental implant according to claim 2, wherein said front surfaces are inclined rearwardly obliquely from their outer circumferences.

4. A dental implant according to claim 3, wherein said obliquely oriented front surfaces are oriented at an angle of from 10 to 60 degrees relative to a plane disposed perpendicularly to said longitudinal axis.

5. A dental implant according to claim 4, wherein said angle is 15 degrees.

6. A dental implant according to claim 1, wherein said at least one surface comprises said rear surface.

7. A dental implant according to claim 6, wherein said rear surfaces are inclined forwardly obliquely from their outer circumferences.

8. A dental implant according to claim 7, wherein said obliquely inclined rear surfaces are oriented at an angle of from 10 to 60 degrees relative to a plane disposed perpendicularly to said longitudinal axis.

9. A dental implant according to claim 7, wherein said angle is 15 degrees.

10. A dental implant according to claim 1, wherein said at least one surface comprises both said front and rear surfaces.

11. A dental implant according to claim 1, wherein said body includes a divider wall separating said front and rear cavities.

12. A dental implant according to claim 1, including a plurality of ribs disposed longitudinally between longitudinally spaced ones of said through-holes.

13. A dental implant according to claim 1, wherein said ribs extend circumferentially endlessly.

* * * * *